United States Patent [19]

Grossman et al.

[11] 4,219,029
[45] Aug. 26, 1980

[54] FEMALE BREAST VOLUME MEASURING DEVICE

[76] Inventors: Jack Grossman; Leonard A. Roudner, both of 505 N. Lake Shore Dr., Chicago, Ill. 60611

[21] Appl. No.: 18,145

[22] Filed: Mar. 7, 1979

[51] Int. Cl.³ .............................................. A61B 5/10
[52] U.S. Cl. ................................... 128/774; 33/2 R; 33/174 D; 73/149
[58] Field of Search ........ 128/774, 771, 767, 280–282; 33/174 D, 2 R; 73/149, 429; 3/36

[56] References Cited

U.S. PATENT DOCUMENTS

| | | | |
|---|---|---|---|
| 716,613 | 12/1902 | Anderson | 33/2 R |
| 1,048,929 | 12/1912 | Baird | 33/2 R |
| 2,527,206 | 10/1950 | Amyot | 33/174 D X |
| 2,559,501 | 7/1951 | Graf | 33/174 D |
| 2,725,633 | 12/1955 | Graf | 33/2 R |
| 2,946,125 | 7/1960 | Gittelson | 33/2 R |
| 3,292,261 | 12/1966 | Hayes | 33/2 R |
| 4,024,856 | 5/1977 | Kirianoff | 128/774 |
| 4,131,998 | 1/1979 | Spears | 128/774 X |

FOREIGN PATENT DOCUMENTS

| | | | |
|---|---|---|---|
| 1521348 | 3/1968 | France | 3/36 |

*Primary Examiner*—Kyle L. Howell
*Attorney, Agent, or Firm*—Silverman, Cass & Singer, Ltd.

[57] ABSTRACT

A device for measuring the volume of a female breast.

In one embodiment, a circular template or sheet of transparent, flexible material is capable of being formed into a hollow cone whose size can be adjusted. Calibrations are provided selectively for indicating a series of breast volume measurements directly. In use, the sheet is formed into a cone around the breast and adjusted in position to conform to the compressed configuration of the breast. The volume of the breast contained in the cone is then read directly from the calibrations on the sheet.

In another embodiment, a rectangular template or sheet of transparent flexible material is capable of being formed into a hollow cylinder which can be adjusted in diameter selectively. Calibrations are provided on the sheet for indicating the inside volume of the cylinder at different locations along its length for different inside diameters of the cylinder. A plunger or disk is provided which is sized to move inside the cylinder. In use, the sheet is formed into a cylinder around the breast, adjusted in diameter to contain the breast tightly and then locked at that position. The plunger or disk is then inserted into the cylinder and pressed against the breast lightly so as to compress the breast completely to fill the cylinder. The volume of the cylinder filled by the compressed breast is then read directly from the calibrations on the sheet.

16 Claims, 9 Drawing Figures

FEMALE BREAST VOLUME MEASURING DEVICE

BACKGROUND OF THE INVENTION

This invention relates generally to a device for measuring the volume of a female breast and, more particularly, to a device of the character described formed of a transparent flexible sheet material capable of measuring breast volume of a great range of sizes conveniently, accurately and with highly desired accommodation of the female being measured.

It is not uncommon for women to have cosmetic surgery performed on their breasts. In one such type of operation known as a "mastopexy", the breasts are elevated to provide a more youthful and/or attractive appearance. In another type of operation known as "augmentation mammaplasty", material is implanted into one or both of the breasts for the purpose of increasing their size. In still another type of operation known as "reduction mammaplasty", tissue is removed from one or both of the breasts for the purpose of decreasing their size.

Surgery is also performed on the breasts for medical reasons. In one such type of operation known as a "mastectomy", the breast or a portion thereof is removed. In the breast reconstruction following a mastectomy, if breast reconstruction is in fact possible, material is inserted into the portion of the breast remaining after the surgery to restore the breast to its original size and/or appearance.

In each one of these operations it is extremely important for the breast surgeon to be able to accurately determine the volume of the breasts before, during and after the surgery. Quite frequently, the breasts are not of equal volumetric size. By knowing the exact volume of each breast, the amount of material that need be added or removed from each breast to produce breast symmetry can be easily determined.

Accurate volumetric size of a woman's breasts is useful for reasons other than surgical. Many women often wish to know their personal breast volume as a means of monitoring weight changes and growth or bust development. In addition, such information is useful in connection with the fitting of a brassiere.

Thus, the need exists for an easily and conveniently usable device by means of which the volume of a woman's breasts can be accurately measured.

In the past, various techniques have been employed for determining the volumetric size of a woman's breasts. For the most part, however, these techniques have proven to be inadequate from a technical standpoint, cumbersome or complex, or personally objectionable to the female whose breasts were being measured.

One prior technique has been to estimate the size by visual means. This technique is obviously imprecise. Another technique has been to use the brassiere breast cup size as the criteria. This is also imprecise since brassiere breast cups are generally made only in four different sizes and, consequently, will not provide exact measurements. Furthermore, breast cup sizes and shapes have a tendency to vary with the manufacturer of the brassiere. Also it is somewhat difficult to determine to what extent the breast actually fills the cup.

One prior art apparatus utilized a plastic container having a discharge orifice filled with a liquid. The breast was lowered into the container by having the woman bend over the container from an upright or seated position. The volume of liquid displaced by the breast provided the measurement of the breast volume. One of the problems attendant this type of apparatus was that it is sometimes difficult to produce total immersion of the breast in the liquid because of the tendency of the breast to float. Consequently, the indicated volume tended to be less than the actual volume. U.S. Pat. No. 2,559,501 taught this apparatus.

Another prior art apparatus used a concave template of fixed size and shape placed around the breast and releasably sealed to the chest. A liquid was injected into the template. The amount of liquid that was injected in the space in the template not occupied by the breast was measured. From this measurement, the breast volume was calculated. One of the problems with this type of apparatus was that it was difficult to effect a perfect seal of the template to the chest, which is necessary to prevent the liquid from escaping. U.S. Pat. No. 4,024,856 taught this apparatus.

In another prior apparatus, the breast was drawn into one end of a fixed diameter glass or rigid plastic tube having graduations indicating the inside volume. A plunger was inserted into the tube from the other end and the breast compressed until it filled the shape of the tube. One of the problems with this type of apparatus was that the amount of pressure needed to compress small sized non-cylindrically shaped breasts to conform to the cylindrically shaped cavity of the tube or to force very large size breasts into the tube was excessive and, thus, uncomfortable to the woman being measured.

Furthermore, none of these apparatus is particularly suited for personal use by the woman.

SUMMARY OF THE INVENTION

The purpose of this invention is to provide a device for measuring the volume of a female breast that is simple to use, accurate and economical, that can be used by a breast surgeon in connection with various types of operations performed on the breasts and that can be used by women for their personal breast size determinations conveniently. The device is characterized as being selectively adjustable to contain a breast in a suitably compressed configuration which can be measured volumetrically by calibration indicia on the device.

In one embodiment of the invention which is particularly useful with small volume breasts, the device comprises a flat, circular sheet of transparent, flexible material which can be formed into a cone whose internal size is adjustable. Calibrations are provided along one edge of the sheet for indicating volumetric measurements directly. In use, the flat sheet is formed into a cone around the breast and adjusted in size so that it compresses the breast to fill the conical volume desired. The volume of the cone is then read from the calibrations to provide breast volume measurement directly.

In a second embodiment of the invention, which is intended primarily for larger or fuller breasts but not exclusively limited for use therewith, the device comprises a rectangular sheet of transparent, flexible material that can be formed into a hollow cylinder whose diameter is adjustable. The device further includes a disk or plunger adapted to be moved inside the cylinder so formed. Calibrations are provided on the cylinder indicating the volume inside the cylinder at different locations along its length for different diameters to which the cylinder is formed. Means are provided for locking the cylinder at any adjusted size. In use, the sheet is formed into a cylinder around the breast, adjusted in cross-sectional area to conform to the configuration of the breast and then locked at that position. The disk is then inserted into the cylinder and lightly pressed against the breast until the breast conforms to or fills the cylindrical shape. The volume of the breast, that is, the portion of the cylinder occupied by the breast, is read directly from the calibrations on the cylinder. Since the cross-sectional area of the cylinder can be adjusted to the approximate size of the breast, the amount of pressure that need be applied to the breast to compress it to a cylindrical shape is not very great.

Both embodiments of the device can be easily disassembled after the measurement is made, cleaned and stored for re-use. In fact, the economical character of the device lends to the invention the capability of being disposable after each use.

BRIEF DESCRIPTION OF THE DRAWINGS

In the drawings wherein like reference numerals represent like parts.

DESCRIPTION OF PREFERRED EMBODIMENTS

Figure 1:
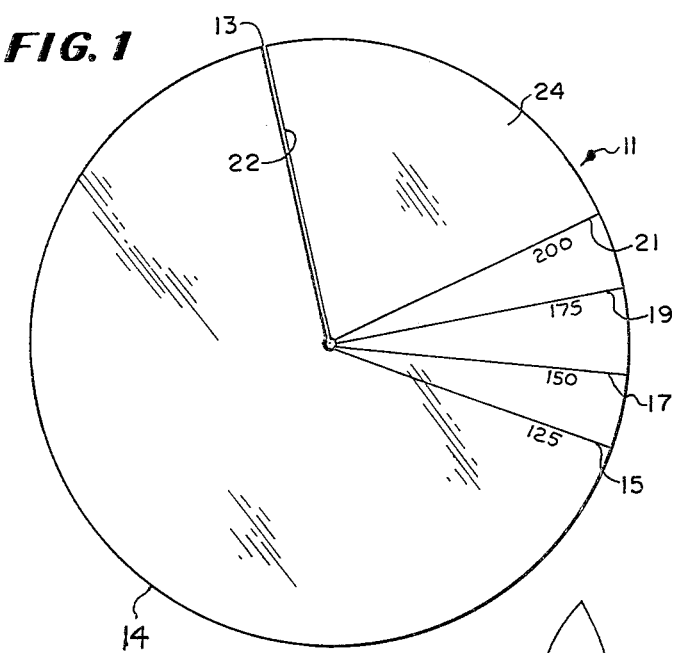
FIG. 1 is a plan view of a template or sheet blank for forming one embodiment of a device for measuring the volume of a female breast according to this invention.

Referring now to the drawings, there is shown in FIG. 1 a blank designated by reference numeral 11.

Blank 11 comprises a circular sheet of transparent, flexible material such as plastic. A radial cut or slot 13 extends from the center of the sheet to the periphery 14. A plurality of calibrations 15, 17, 19 and 21 extend radially outward from the center. The calibrations, which are imprinted or formed by any other suitable means, indicate the volume in milliliters when blank 11 is formed into a cone 25. Blank 11 is formed into cone 25 by slidably moving the edge 22 of blank 11 on one side of slot 13 over on the body portion 24 of blank 11 on the opposite side of slot 13. The volumetric size of the resulting cone 25 is adjusted by sliding edge 22 over body portion 24 so as to vary the circumference of the cone 25, by varying the amount of overlap between the two portions, and align said edge with a calibration.

Figure 2:
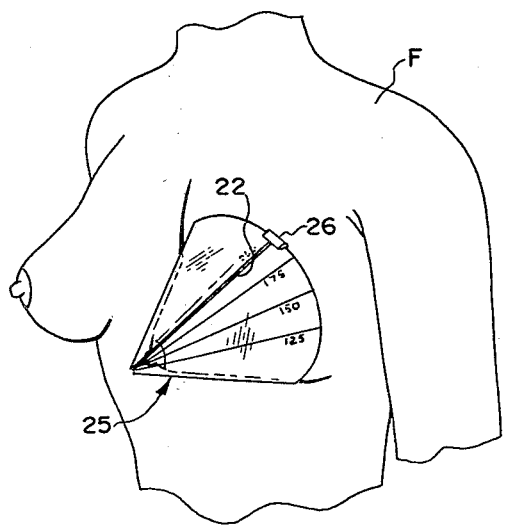
FIG. 2 is a perspective view of the device formed from the template of FIG. 1, illustrating how the device is applied to the breast.
Figure 3:
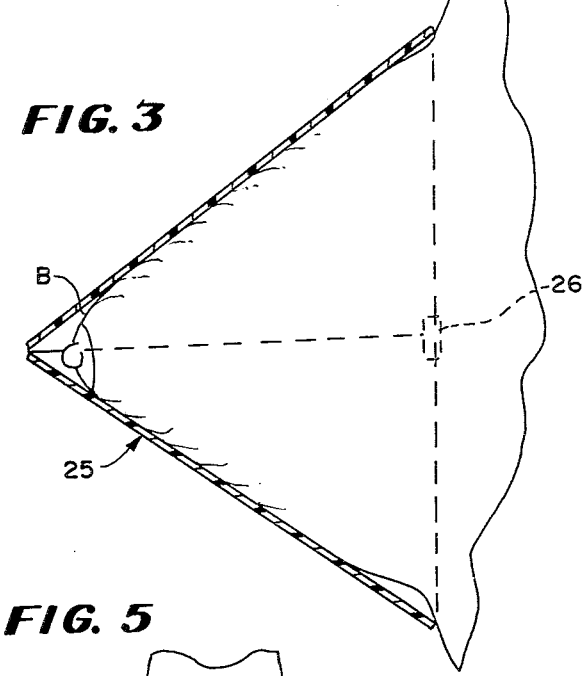
FIG. 3 is a vertical sectional view taken through the device as shown installed in FIG. 2.

To use blank 11 to measure the volume of a female breast, blank 11 is first formed into cone 25 around the breast B of the female F, as shown in FIGS. 2 and 3, with the female in either a sitting or standing position. Then, the size of the cone is adjusted by sliding edge 22 over portion 24 until the volume inside the cone is substantially filled by the breast. The volume of the cone so formed, and correspondingly, the volume of the breast contained within the cone, is then read directly from the calibrations, using edge 22 of slot 13 as the index line. The cone shaped breast measuring device formed by blank 11 is particularly suited for use with small and/or conical shaped breasts but is not exclusively limited to use with such breast configurations.

Since the sheet 11 is flexible, it can be manipulated to form the measuring cone 25 easily and readily without unnecessary contact with the breast. The transparent character of the cone enables the surgeon to visually check the contents of the cone 25 for accurate measurement determination.

A clip 26 is shown in FIG. 2 which is of channel shape so that the index edge 22 and the thickness of portion 24 can be accommodated therein. The clip 26 assists in maintaining the two parts together for facilitating sliding movement one relative to the other for varying the volumetric size of cone 25.

Figure 4:
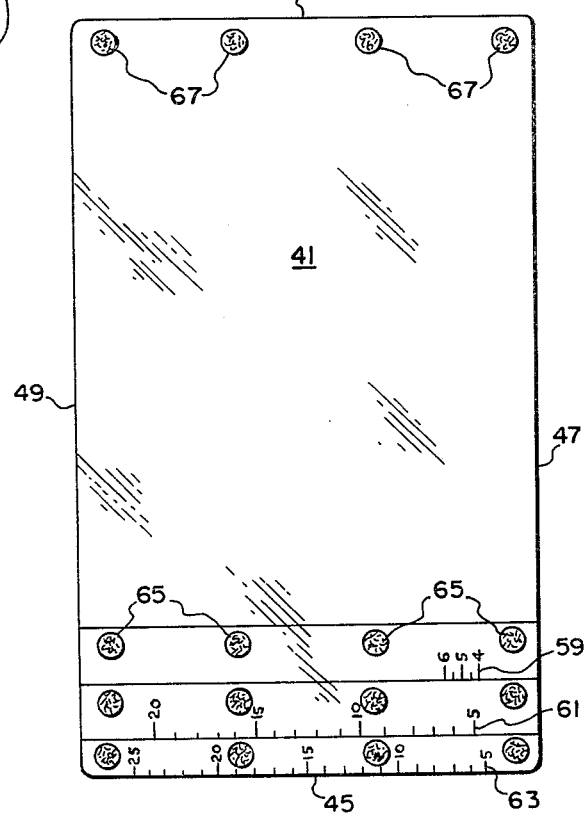
FIG. 4 is a plan view of a template or sheet blank for use in forming a second embodiment of a device for measuring the volume of a female breast according to this invention.

Referring now to FIG. 4, there is shown a blank designated by reference numeral 41 for forming a second embodiment of the device of this invention.

Blank 41 comprises a rectangular sheet of transparent, flexible material such as plastic having a top edge 43, a bottom edge 45, and a pair of side edges 47 and 49. A plurality of rows of calibrations 59, 61 and 63 are formed by imprinting or any other suitable means at the bottom of blank 41 adjacent and parallel to bottom edge 45. Each row of calibration is arranged to indicate the volume in milliliters, when blank 41 is formed into a hollow cylinder 64, of the space between edge 47 and locations at various distances from edge 47. A plurality of locking tabs 65 are mounted along the front side of blank 41 along rows of calibrations 59, 61 and 63 and another group of locking tabs 67 adapted to mate with tabs 65 are mounted in a row on the rear side of blank 41 near top edge 43. The purpose of tabs 65 and 67 is to lock the cylinder so formed at a particular cross-sectional size. Such tabs are formed of a material known by the trademark "VELCRO".

Blank 41 is formed into cylinder 64 by bending or rolling blank 41 so that edge 47 extends over edge 49. The size of the resulting cylinder, that is the circumference or cross-sectional diameter, is adjusted by varying the amount of the overlap.

Figure 5:
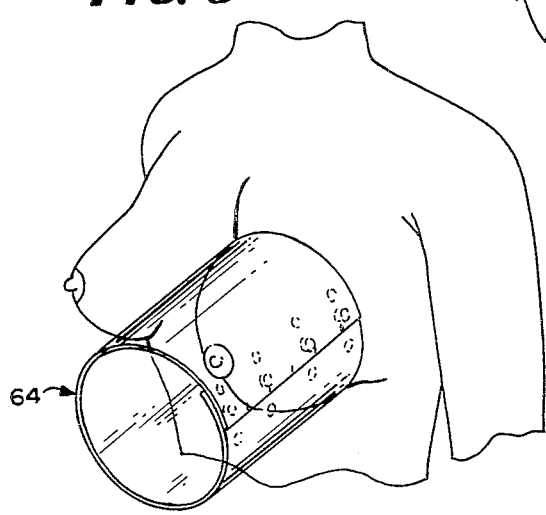
FIG. 5 is a perspective view illustrating how the blank in FIG. 4 is erected and applied to the breast.
Figure 6:
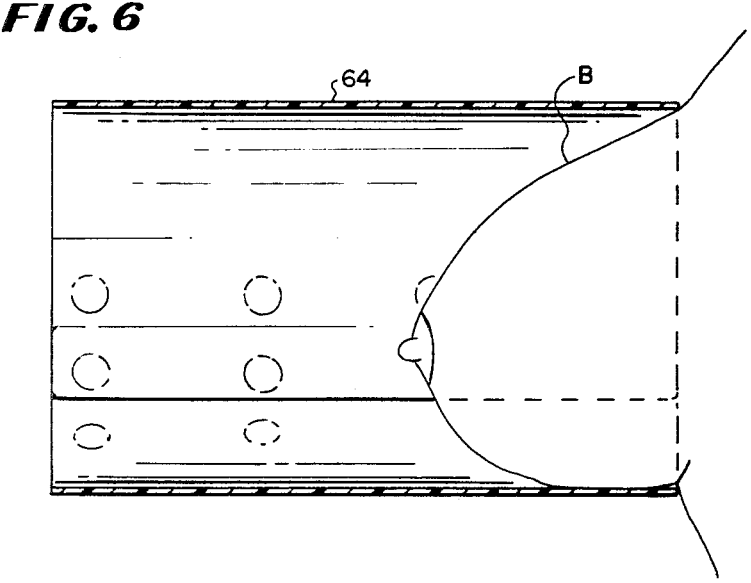
FIG. 6 is a sectional view taken through the blank as shown applied to the breast in FIG. 5, with the breast in a relaxed position.
Figure 7:
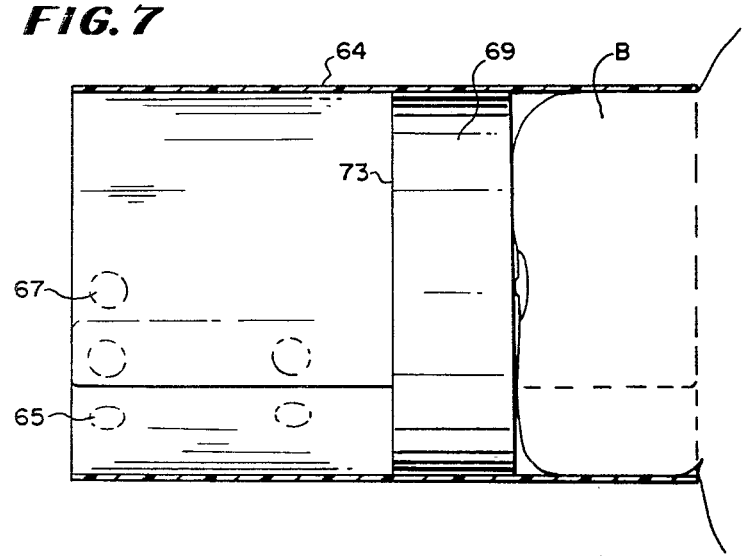
FIG. 7 is a vertical sectional view of a second embodiment of a device for measuring the volume of a female breast, with the device in position and the breast in a compressed configuration.

To use blank 41 to measure the volume of a female breast, blank 41 is first formed into cylinder 64 around the breast as shown in FIG. 5, with the female in either a sitting or standing position. Then, the diameter of the cylinder is adjusted until its cross-sectional area corresponds to the size of the breast as shown in FIG. 6. The cylinder so formed is then locked at that particular size by pressing the Velcro tabs 67 against the appropriate row of Velcro tabs 65. Then, a rigid disk 69 having a flat front surface 71 is inserted into the cylinder from the end opposite the end containing the breast and lightly pushed against the breast until the breast is compressed to conform to the shape of the cylinder as shown in FIG. 7. The volumetric measurement of the breast is then directly read from the calibrations using the front edge of the disk 69 as the index line.

Disk 69 may be made of plastic or other suitable material and may include finger gripping means such as indentations on its rear surface 73. Disk 69 is sized so that it will fit into and be able to move within the various sized cylinders that can be formed by blank 41.

Figure 8:
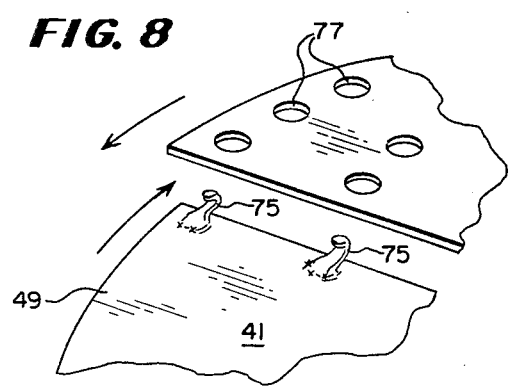
FIG. 8 is a fragmentary perspective view illustrating an alternate form of locking means for locking the device of FIG. 6 in a selected volumetric measurement configuration.
Figure 9:
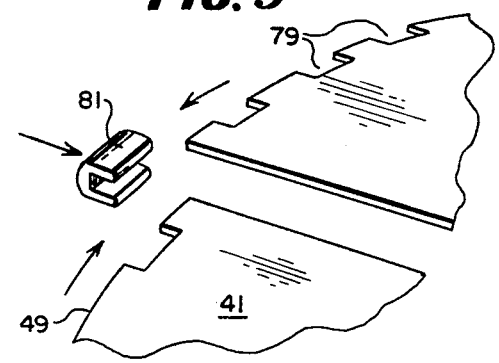
FIG. 9 is a fragmentary perspective view of another form of locking means of the device of FIG. 6.

Instead of Velcro tabs, blank 41 may be locked at a particular size by a row of hooks 75 attached to blank 41 near top edge 43 which engage one of a plurality of rows of holes 77 formed near bottom edge 45 as shown in FIG. 8. In still another arrangement, the side edges 47 and 49 of blank 41 may be formed with slots 79 and the cylinder fixed at a particular size by clips 81 which fit into overlapping slots as illustrated in FIG. 9. These alternate locking arrangements may also be used in connection with the FIG. 2 embodiment.

It may be appreciated from the foregoing specification that the embodiments of the invention each enable a woman to measure her own breast volume privately. Further, the devices cover a range of normally expected breast volume measurements adequately and comprehensively.

To produce the two embodiments described and illustrated, we provide a chart of calibrations and angular designations correlated to the volumetric measurement calibrations (in milliliters) as follows:

For the cone embodiment 25:

| For the cone embodiment 25: | | Volume (ml) | Angle |
|---|---|---|---|
| A. | Small cone (R = 8 cm.) | 125 | 130° |
| | | 150 | 110° |
| | | 175 | 90° |
| | | 200 | 75° |
| B. | Medium cone (R = 9 cm.) | 200 | 145° |
| | | 225 | 130° |
| | | 250 | 115° |
| | | 275 | 90° |
| | | 300 | 75° |
| C. | Large cone (R = 10 cm.) | 300 | 130° |
| | | 325 | 120° |
| | | 350 | 110° |
| | | 375 | 95° |
| | | 400 | 85° |
| | | 425 | 65° |

For embodiment 64, the calibrations are also indicated in 100 milliliters. Thus, the volumetric breast measurements for this embodiment range from 400 to 2500 milliliters.

It is to be understood that various changes and modifications may be made without departing from the spirit or scope of the invention as set forth in the appended claims.

What is claimed is:

1. A device for measuring the volume of a female breast comprising an elongated hollow member of a flexible sheet material adapted to be engaged around and completely enclose a breast whose volume is to be measured, said elongated hollow member being adjustable in circumference to conform the cross-sectional area of the hollow member to a received breast, and having calibrations on a body portion thereof and an indexing means capable of being selectively aligned with a calibration for indicating the volumetric measurement of the breast contained therein.

2. The device according to claim 1 wherein the elongated hollow member is transparent so that the breast contained therein can be observed for obtaining accurate measurement.

3. The device according to either claims 1 or 2 wherein the elongated member is shaped to define a cone whose inside volumetric size is adjustable.

4. The device according to either claims 1 or 2, including means for releasably locking the member in a selected size configuration for breast measurement.

5. The device of claim 1 wherein the elongated hollow member is constructed and arranged to define a cylinder whose cross-sectional area is adjustable.

6. The device of claim 5 wherein the elongated hollow member comprises a rectangular sheet of transparent flexible material arranged to form the cylinder.

7. The device of claim 6 including means for releasably securing the member at a selected cross-sectional area.

8. The device of claim 7 including a flat member slidably movable inside the cylinder for use in selectively compressing the breast contained therein into a cylindrical shape to provide volumetric measurement thereof directly coinciding with the calibration aligned with said flat member.

9. A device for measuring the volume of a female breast comprising an elongated hollow member formed of a flexible sheet material open at one end thereof and adapted to receive a breast whose volume is to be measured, said elongated hollow member being adjustable in cross-sectional area, and having calibrations on a body portion thereof and an indexing means capable of being selectively aligned with a calibration for indicating the volumetric measurement of the breast contained therein, the elongated hollow member comprising a piece of transparent, flexible sheet material circular in shape and having a radial slot, a portion of the sheet on one side of the slot extending over a portion of the sheet on the other side of the slot so as to form a cone whose interior volumetric size is adjustable.

10. The device according to claim 9 including clip means for slidably receiving said portions of the member on opposite sides of said slot.

11. A device for measuring the volume of a female breast comprising a circular sheet of flexible transparent material adapted to be selectively formed about a breast into a cone open at one end and completely enclosing the breast, said sheet of material being adjustable to vary the cross-sectional area and interior volume of the cone, calibrations on said sheet of material indicating the interior volume size of the cone so formed and means for releasably holding the sheet in the shape of a cone at a preselected volumetric size thereof coinciding with the volumetric size of a breast received therein.

12. A device for measuring the volume of a female breast comprising a rectangular sheet of flexible transparent material adapted to be formed about a breast and into a diametrically adjustable cylinder completely enclosing the breast, said cylinder having a variable cross-sectional area and interior volume, the cylinder being open at both ends, calibrations on said sheet of material indicating the volume inside the cylinder so formed at different locations along its length according to its cross-sectional size and means for releasably locking the sheet in the shape of a cylinder at a preselected size indicating the volumetric measurement of a breast contained therein.

13. The device of claim 12 and further including means adapted to be inserted in the cylinder so formed for compressing a breast inserted therein into the shape of the cylinder.

14. A device for measuring the volume of a female breast comprising a rectangular sheet of flexible transparent material adapted to be formed into a cylinder whose cross-sectional area is adjustable and is open at both ends, calibrations on said sheet of material indicating the volume inside the cylinder so formed at different locations along its length according to its cross-sectional size, means adapted to be inserted in the cylinder so formed for compressing a breast inserted therein into the shape of the cylinder, and cooperating means for releasably locking the sheet in the shape of a cylinder at a preselected size indicating the volumetric measurement of a breast contained therein, said cooperating means comprising engaging tabs of friction material.

15. A device for measuring the volume of a female breast comprising a rectangular sheet of flexible transparent material adapted to be formed into a cylinder whose cross-sectional area is adjustable and is open at both ends, calibrations on said sheet of material indicating the volume inside the cylinder so formed at different locations along its length according to its cross-sectional size, means adapted to be inserted in the cylinder so formed for compressing a breast inserted therein into the shape of the cylinder, and cooperating means for releasably locking the sheet in the shape of a cylinder at a preselected size indicating the volumetric measurement of a breast contained therein, said cooperating means comprising hook and eye members.

16. A device for measuring the volume of a female breast comprising a rectangular sheet of flexible transparent material adapted to be formed into a cylinder whose cross-sectional area is adjustable and is open at both ends, calibrations on said sheet of material indicating the volume inside the cylinder so formed at different locations along its length according to its cross-sectional size, means adapted to be inserted in the cylinder so formed for compressing a breast inserted therein into the shape of the cylinder, and cooperating means for releasably locking the sheet in the shape of a cylinder at a preselected size indicating the volumetric measurement of a breast contained therein, said cooperating means comprising slots formed in side edges of the sheet and clip members matingly engaged in said slots.

* * * * *